US010582990B2

(12) United States Patent
Dai et al.

(10) Patent No.: US 10,582,990 B2
(45) Date of Patent: Mar. 10, 2020

(54) HEAD MODULE CAPABLE OF RECIPROCAL ROTATION FOR ELECTRIC CLEANING APPARATUS

(71) Applicant: SHANGHAI SHIFT ELECTRICS CO., LTD., Shanghai (CN)

(72) Inventors: Xiaoguo Dai, Shanghai (CN); Zhenwu Xu, Shanghai (CN)

(73) Assignee: SHANGHAI SHIFT ELECTRONICS CO., LTD., Shanghai (CN)

( * ) Notice: Subject to any disclaimer, the term of this patent is extended or adjusted under 35 U.S.C. 154(b) by 44 days.

(21) Appl. No.: 15/779,075

(22) PCT Filed: Nov. 25, 2015

(86) PCT No.: PCT/CN2015/095484
§ 371 (c)(1),
(2) Date: May 24, 2018

(87) PCT Pub. No.: WO2017/088113
PCT Pub. Date: Jun. 1, 2017

(65) Prior Publication Data
US 2018/0311022 A1 Nov. 1, 2018

(51) Int. Cl.
*A61C 17/34* (2006.01)
*A61C 17/22* (2006.01)
*A46B 5/00* (2006.01)

(52) U.S. Cl.
CPC .......... *A61C 17/222* (2013.01); *A46B 5/0095* (2013.01); *A61C 17/225* (2013.01); *A61C 17/3418* (2013.01); *A61C 17/34* (2013.01)

(58) Field of Classification Search
CPC ....... A61C 17/22; A61C 17/222; A61C 17/34; A61C 17/225
See application file for complete search history.

(56) References Cited

U.S. PATENT DOCUMENTS 6,381,795 B1 * 5/2002 Hofmann .............. A61C 17/22
15/28
2001/0014990 A1 * 8/2001 Fritsch .................. A61C 17/22
15/28
(Continued)

FOREIGN PATENT DOCUMENTS

CN 2626456 Y 7/2004
CN 101902986 A 12/2010
(Continued)

OTHER PUBLICATIONS

International Patent Application No. PCT/CN2015/095484; Int'l Search Report; dated Jun. 27, 2016; 3 pages.
(Continued)

Primary Examiner — Michael D Jennings
(74) Attorney, Agent, or Firm — BakerHostetler

(57) ABSTRACT

A head module capable of reciprocal rotation for an electric cleaning apparatus comprises cleaning elements, a housing and a driven rod disposed in a hollow inner cavity of the housing, wherein the rod is provided with a hollow cavity body for accommodating a drive shaft; at least one gap is provided in a region surrounding the hollow cavity body; at least one inner side notch is distributed on a side wall of the inner cavity, for accommodating a protrusion; the rod further comprises a partially cylindrical or conical cavity body region. When the drive shaft is not yet inserted into the rod, there is a gap between the notch and the protrusion in a direction perpendicular to the rotation axis (L1) of the drive shaft. The length of the gap is greater than or equal to the amount of single-side interference between the rod and the drive shaft.

22 Claims, 13 Drawing Sheets

(56) References Cited

U.S. PATENT DOCUMENTS

| | | | | |
|---|---|---|---|---|
| 2010/0043156 A1* | 2/2010 | Kressner | ............... | A61C 17/222 15/22.1 |
| 2010/0101032 A1* | 4/2010 | Kressner | ................ | A61C 17/22 15/22.1 |
| 2014/0165312 A1 | 6/2014 | Fattori | | |

FOREIGN PATENT DOCUMENTS

| | | |
|---|---|---|
| CN | 202446287 U | 9/2012 |
| CN | 203059955 U | 7/2013 |
| CN | 203315105 U | 12/2013 |
| CN | 104135964 A | 11/2014 |
| CN | 104352057 A | 2/2015 |
| CN | 105411713 A | 3/2016 |
| CN | 205181511 U | 4/2016 |
| DE | 19745876 A1 | 4/1999 |
| WO | WO 2012/042427 A2 | 4/2012 |
| WO | WO 2013/009362 A1 | 1/2013 |

OTHER PUBLICATIONS

European Patent Application No. 15909025.7; European Search Report; dated Oct. 4, 2018; 10 pages.

* cited by examiner

HEAD MODULE CAPABLE OF RECIPROCAL ROTATION FOR ELECTRIC CLEANING APPARATUS

CROSS-REFERENCE TO RELATED APPLICATIONS

This application is a U.S. national phase application of International Application No. PCT/CN2015/095484, filed on Nov. 25, 2015, the entirety of which is incorporated herein by reference.

TECHNICAL FIELD

The present invention relates to a head module capable of reciprocal rotation for an electric cleaning apparatus, and more specifically, to a head module capable of reciprocal rotation for an electric cleaning apparatus, having a security structure that can prevent the head module from being detached from a handle during an operation of the cleaning apparatus.

BACKGROUND

In the electric cleaning apparatus, a torque of a drive shaft is often reliably transmitted to a head for cleaning by means of an interaction between the drive shaft and a coupling structure, and the torque transmission is maintained under load. In addition, the interaction between the drive shaft and the coupling structure must ensure keeping the head on the drive shaft during the operation of the cleaning appliance, and allowing a user to conveniently remove the head from the drive shaft when the cleaning apparatus is not operated.

For example, the invention patent with the authorization announcement number CN101902986 B discloses a brush head/handle interface for an electric toothbrush, comprising: a brush head assembly having a brush member at one end thereof for cleaning teeth; a drive shaft extending from a handle portion of the toothbrush and driven to oscillates through a selected rotational angle, the drive shaft having one or more contact regions in which are located interface surfaces; a coupling member positioned at the other end of the brush head assembly and having a body portion, wherein the coupling member includes one or more interface portions which come into physical contact with said interface surfaces of the drive shaft when the drive shaft is inserted into the coupling member; and a spring member positioned around a part of the body portion so as to exert a sufficient force on the body portion and the coupling member large so that the physical contact between said interface portion or portions of the coupling member and said one or more contact regions of the drive shaft is sufficient to maintain actual retention of the brush head assembly on the drive shaft during operation of the toothbrush, while permitting a user to remove the brush head assembly from the drive shaft when the toothbrush is not operating.

SUMMARY

The object of the present invention is to provide a head module capable of reciprocal rotation for an electric cleaning apparatus, having a novel security structure that can ensure the head module not to be detached from a handle during an operation of the cleaning apparatus. In addition, the head module also has the advantages of small volume, simple structure, long service life, and easy assembly and operation.

The head module capable of reciprocal rotation for an electric cleaning apparatus according to the present invention is detachably coupled to a handle, and a drive shaft in the handle extends upward out of the handle in a direction of its rotation axis and reciprocally rotates around its rotation axis to thereby drive the head module to make a reciprocal rotation movement around the rotation axis of the drive shaft. The head module comprises cleaning elements, a head module housing and a head module driven rod disposed in a hollow inner cavity of the head module housing, wherein the head module driven rod is provided with a hollow cavity body of the head module driven rod for accommodating the drive shaft, and at least one gap of the head module driven rod is provided in a region surrounding the hollow cavity body so that the head module driven rod has elasticity in the radial direction of the cross section of the hollow cavity body of the head module driven rod; at least one inner side notch of the head module housing is distributed on a side wall of the inner cavity of the head module housing, and the inner side notch is used for accommodating a corresponding protrusion of the head module driven rod disposed on the head module driven rod so that the inner side notch of the head module housing restricts a movement of the protrusion of the head module driven rod in the direction of the rotation axis of the drive shaft; the head module driven rod further comprises a partially cylindrical or conical cavity body region, and a diameter of the cylindrical or conical cavity body region or the greatest diameter of a corresponding joining portion is less than a diameter of a cylinder or conoid region of the drive shaft or the greatest diameter of a corresponding joining portion, both (the cylindrical or conical cavity body region of the head module driven rod or a corresponding joining portion and a cylinder or conoid region of the drive shaft or a corresponding joining portion) being an interference fit; when the drive shaft is not yet inserted into the head module driven rod, there is a gap between the inner side notch of the head module housing and the protrusion of the head module driven rod in a direction perpendicular to the rotation axis of the drive shaft, and a length of the gap in the direction perpendicular to the rotation axis of the drive shaft is greater than or equal to the amount of single-side interference between the head module driven rod and the drive shaft, and the amount of single-side interference may be 0.01 mm to 1 mm, preferably 0.20 mm.

The gap of the head module driven rod may be distributed in the head module driven rod in a direction that is not perpendicular to the rotation axis of the drive shaft. Preferably, an included angle between a median line of the gap of the head module driven rod and the rotation axis of the drive shaft is greater than −90 degrees and less than 90 degrees, or the included angle is greater than −45 degrees and less than 45 degrees, or the included angle is zero degree. A width of the gap of the head module driven rod is 0.3 mm-2 mm, preferably 0.7 mm-1.2 mm.

The protrusion of the head module driven rod is located below the top of the gap of the head module driven rod in a direction of the rotation axis of the drive shaft. Two protrusions of the head module driven rod are symmetrically distributed on the head module driven rod along an axis of the head module housing, and the protrusions of the head module driven rod are located below the top of the gap of the head module driven rod in a direction of the rotation axis of the drive shaft, and correspondingly the inner side notch of the head module housing may be disposed on a side wall of the inner cavity of the head module housing. Two inner side notches of the head module housing are symmetrically distributed on the side wall of the inner cavity of the head module housing along the axis of the head module housing.

Each component of the head module is made of plastic.

Two elastic buckles of the head module driven rod with protrusions at the lower end of the elastic buckles are distributed at the lower part of the head module driven rod, and the elastic buckles cooperate with a annular groove of the drive shaft disposed on the drive shaft so that the protrusions at the lower end of the elastic buckles can fully or partially enter the annular groove of the drive shaft, thereby restricting a movement of the head module driven rod relative to the drive shaft in a direction of the rotation axis of the drive shaft of the handle.

According to the present invention, when the drive shaft is inserted into the head module driven rod, since there exists the amount of single-side interference between the head module driven rod and the drive shaft, and due to the elasticity of the protrusion of the head module driven rod formed by the gap of the head module driven rod and the cooperation between the inner side notch of the head module housing and the protrusion of the head module driven rod, the drive shaft can push the protrusion of the head module driven rod deeper into the inner side notch of the head module housing so that the inner side notch of the head module housing more reliably restricts the movement of the protrusion of the head module driven rod along the rotation axis of the drive shaft, thereby ensuring that when the drive shaft is inserted into the head module and starts to drive the head module to make a reciprocal rotation movement, the head module driven rod is undetachably held in the head module housing, thereby effectively preventing the head module housing from leaving the head module driven rod and flying out of the head module driven rod during the movement to injure a user.

According to the present invention, when the drive shaft is inserted into the head module driven rod, since there exists the amount of single-side interference between the head module driven rod and the drive shaft, and due to the elasticity of the protrusion of the head module driven rod formed by the gap of the head module driven rod and the cooperation between the inner side notch of the head module housing and the protrusion of the head module driven rod, the drive shaft can drive the protrusion of the head module driven rod to move in a direction deeper into the inner side notch of the head module housing. A first plane of the head module driven rod and a second plane of the head module driven rod distributed on the head module driven rod move toward or more closely fitted to their respectively matched a first plane of the drive shaft and a second plane of the drive shaft located on the drive shaft, thereby increasing the pressure and friction between the head module driven rod and the drive shaft. During the movement of the head module, the increased friction helps the head module driven rod to always maintain a stable coupling with the drive shaft, thereby preventing the head module from leaving drive shaft and flying out of the drive shaft during the movement to injure the user.

Figure 1:
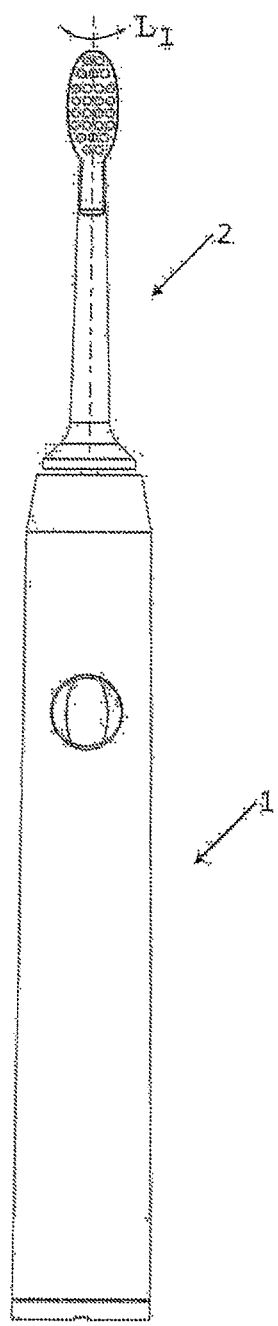
FIG. 1 is a front view of the electric cleaning apparatus (such as an electric toothbrush) of the present invention.

DESCRIPTION OF MAIN REFERENCE NUMERALS 1 handle
2 head module
11 drive shaft
12 handle housing
13 switch button
21 cleaning elements
22 head module housing
23 head module driven rod
111 first plane of the drive shaft
112 annular groove of the drive shaft
113 cylinder region of the drive shaft
114 second plane of the drive shaft
221 inner side notch of the head module housing
222 inner cavity of the head module housing
223 protrusion of the head module housing
224 buckle groove of the head module housing
231 gap of the head module driven rod
232 elastic buckle of the head module driven rod
233 protrusion of the head module driven rod
234 fixing portion of the head module driven rod
235 fixing portion groove of the head module driven rod
236 first plane of the head module driven rod
237 second plane of the head module driven rod
238 partially cylindrical cavity body region of the head module driven rod
239 hollow cavity body of the head module driven rod
240 gap between the head module housing and the head module driven rod
$L_1$ rotation axis of the drive shaft

DETAILED DESCRIPTION

Hereafter, a description will be made to the present invention in more detail with a head module of an electric toothbrush as an example in conjunction with the drawings.

Although the illustration hereinafter is made merely in view of an electric toothbrush, the present invention is not limited thereto. Apparently, the present invention is also applied to other electric cleaning apparatus such as an electric face brush and the like.

In the present invention, the terms indicating spatial relative positions, such as "inside", "outside", "up", "down", "upper (or upper end)", "lower (or lower end)", etc., are used to briefly describe the relationship of one element or feature relative to another element(s) or feature(s) as shown in the drawings. In this description, the terms "inside" and "outside" are defined with respect to the radial direction of the electric cleaning apparatus, where being adjacent to its center is defined as "inside", and being away from its center is defined as "outside"; the terms "up", "down", "upper", "lower", "upper end", "lower end" are defined with respect to the rotation axis of the drive shaft of the electric cleaning apparatus, where the end adjacent to the cleaning elements is defined as "up", "upper" or "upper end", and the end opposite thereto is defined as "down", "lower", or "lower end" when the electric cleaning apparatus works at an upright or inclined state.

When an element is described as "disposed on . . . " or "coupled to" another element, it may be either directly located on or coupled to another element, or there may be intervening element(s) located between the element and the other element. However, when an element is described as "directly disposed on . . . " or "directly coupled to" another element, there is no intervening element(s) located between the element and the other element. As to other wordings and expressions describing the relationship among elements, it will be appreciated that the similar meanings (e.g., "between . . . " corresponding to "directly between . . . ", and the like) are embraced.

Although the terms "first", "second", etc., are used in the present invention to describe a plurality of elements or constituents, these elements or constituents should not to be limited by these words. These words are used simply to distinguish one element or constituent from another element or constituent, without including any "order". Thus, the first element or constituent discussed below referred to as a second element or constituent does not go beyond the concept and scope of the present invention.

Figure 2:
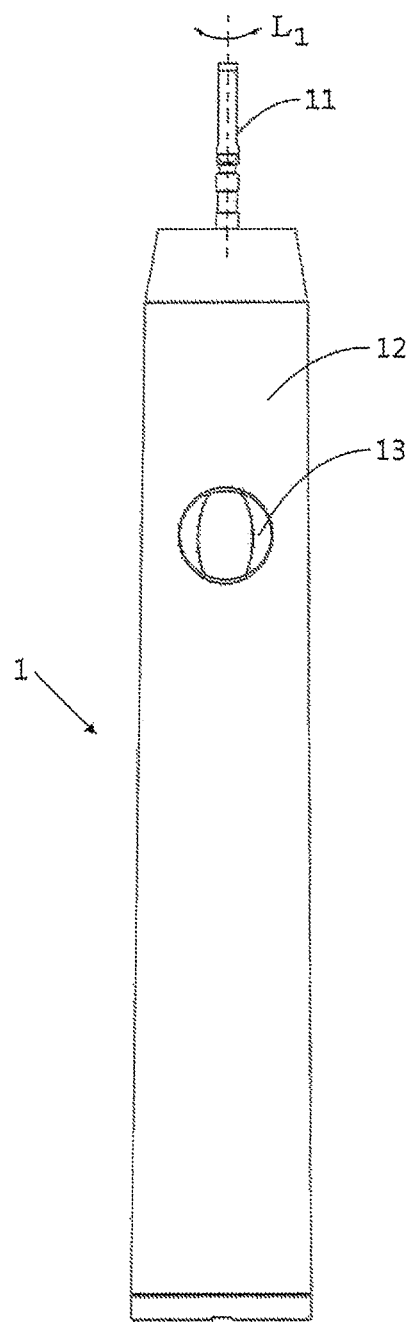
FIG. 2 is a front view of the handle of the electric cleaning apparatus (such as an electric toothbrush) as shown in FIG. 1.
Figure 3:
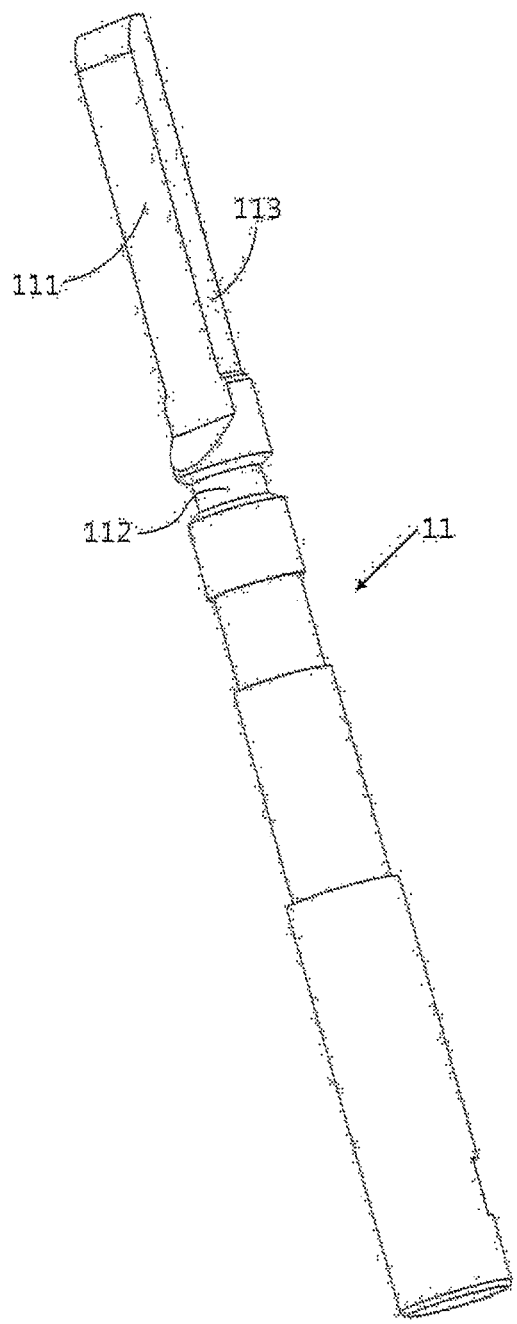
FIG. 3 is a perspective view of the drive shaft fixedly coupled to the handle of the electric cleaning apparatus (such as an electric toothbrush) as shown in FIG. 2, showing the attitude of the drive shaft.
Figure 4:
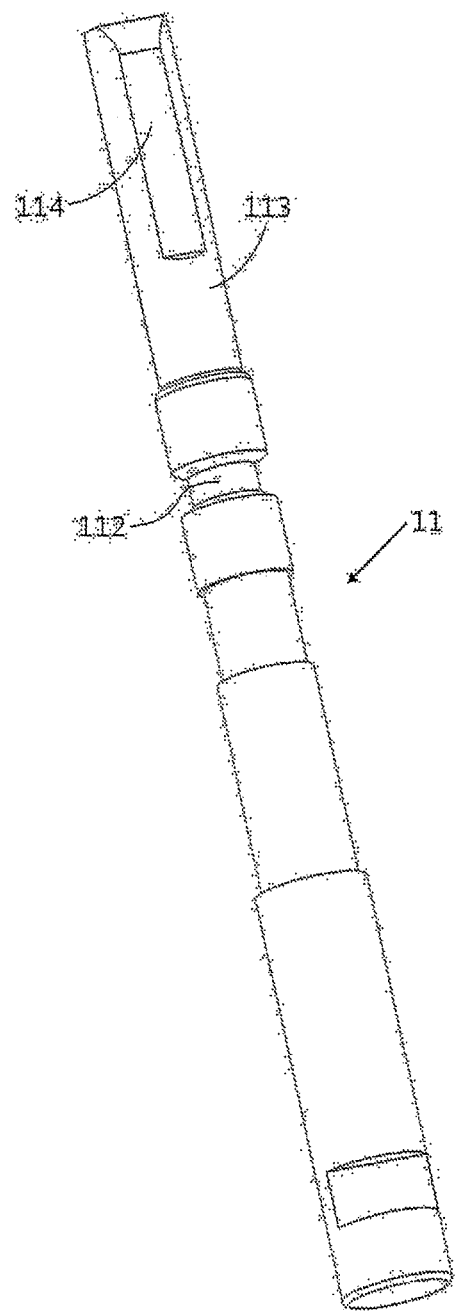
FIG. 4 is another perspective view of the drive shaft fixedly coupled to the handle of the electric cleaning apparatus (such as an electric toothbrush) as shown in FIG. 2, showing the attitude of the drive shaft.

Referring to FIGS. 1 to 7, the electric cleaning apparatus in an embodiment of the present invention includes a handle 1 accommodating a driving portion therein and a head module 2 detachably coupled to the handle 1. A drive shaft 11 (FIG. 2 shows its exposed portion while FIGS. 3 and 4 show the entire drive shaft), which drives the head module 2 to rotate, includes an exposed portion extending upward out of the handle 1 in a direction of rotation axis $L_1$ of the drive shaft. The head module 2 includes: cleaning elements 21, a head module housing 22 and a head module driven rod 23 disposed in the head module housing 22. The head module 2 can be detachably mounted to the handle 1 through cooperation between the head module driven rod 23 and the drive shaft 11, and the drive shaft 11 may reciprocally rotate around the rotation axis $L_1$ of the drive shaft, thereby driving the head module 2 to reciprocally rotate around the rotation axis $L_1$ of the drive shaft.

Referring to FIGS. 3 to 4, the drive shaft 11 is provided with a annular groove 112 of the drive shaft, which divides the drive shaft 11 into upper and lower parts, wherein the lower part may be fixedly coupled to the transmission mechanism in the handle 1 so that the drive shaft 11 can be driven by the transmission mechanism in the handle 1 to reciprocally rotate around the rotation axis $L_1$ of the drive shaft, and wherein the upper part is substantially a cylinder, and the region exhibiting the characteristics of the cylinder is the cylinder region 113 of the drive shaft. The upper part is also provided with a first plane 111 of the drive shaft and a second plane 114 of the drive shaft parallel to each other, that is to say, the upper part is substantially a cylindrical body formed by cutting out two mutually parallel planes. Obviously, the upper part may also be a cone or cuboid formed by cutting out two mutually parallel planes, etc, and the use of a cone or a cuboid does not exceed the scope of the present invention.

Figure 5:
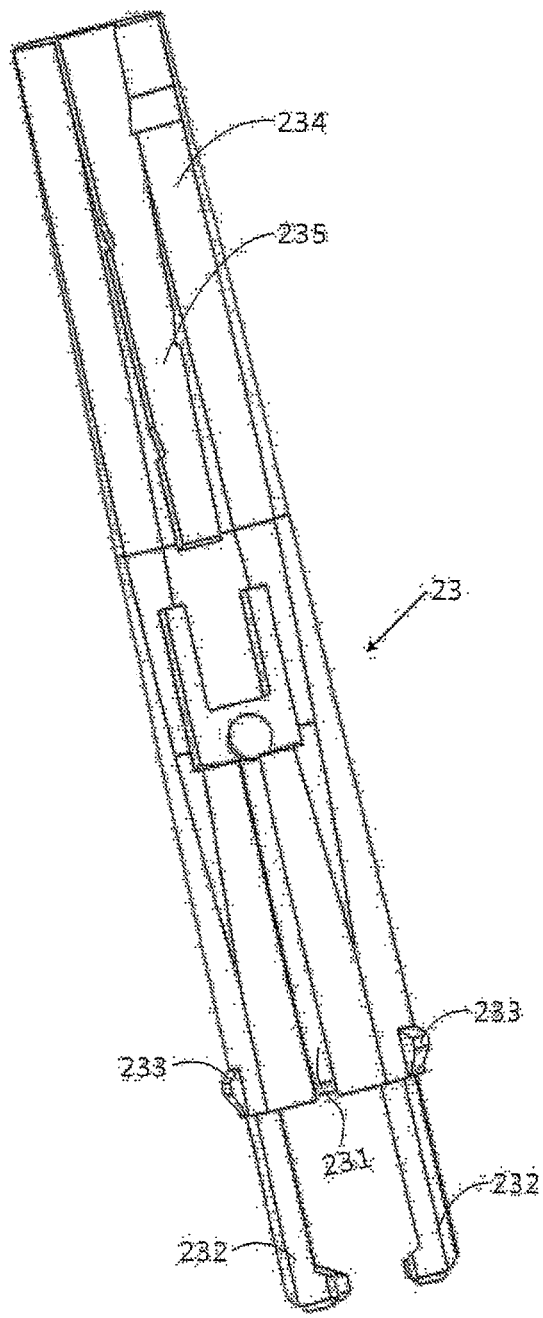
FIG. 5 is a perspective view of the head module driven rod, showing the attitude of the head module driven rod.
Figure 6:
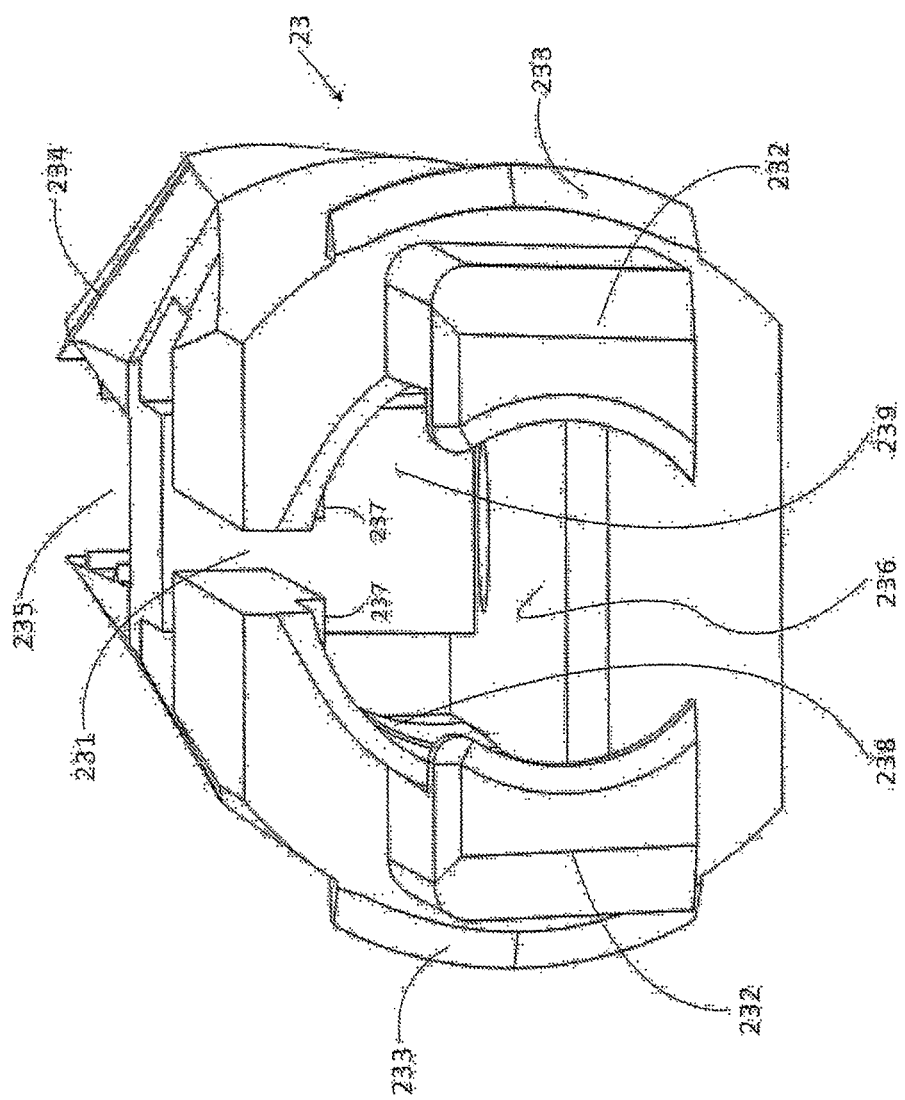
FIG. 6 is a schematic bottom view of the head module driven rod as shown in FIG. 5.
Figure 7:
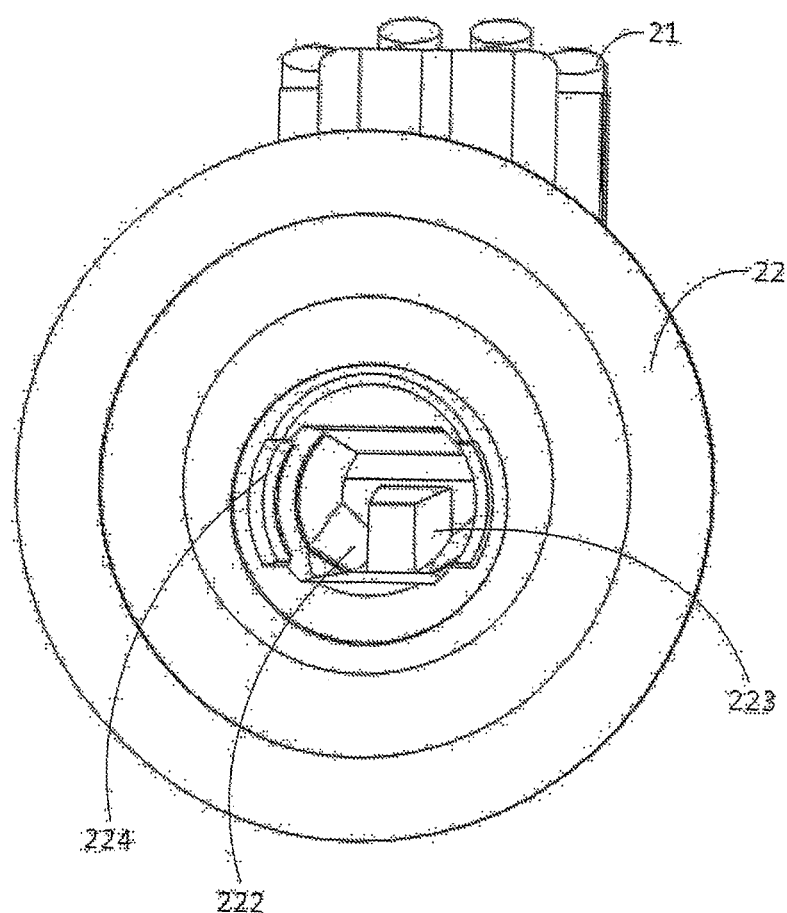
FIG. 7 is a schematic bottom view of the combination of the head module housing and the cleaning elements.
Figure 8:
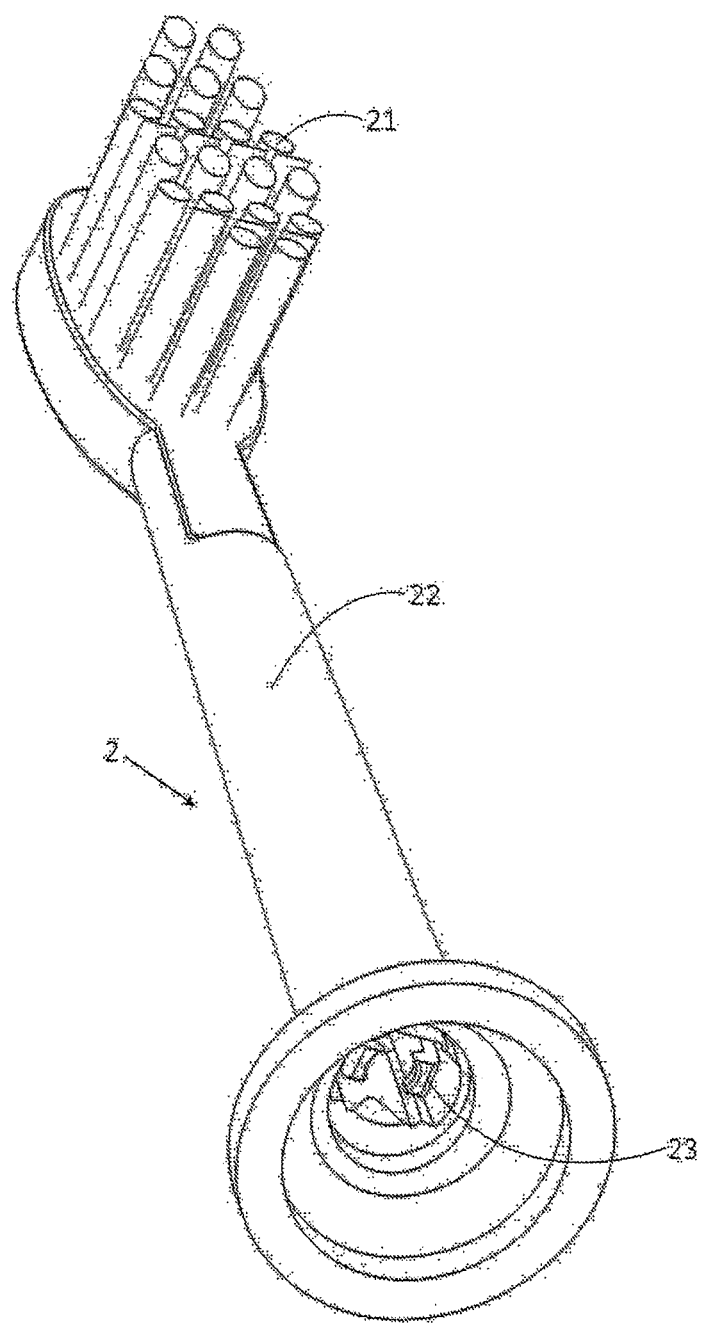
FIG. 8 is a perspective view of the head module of the electric cleaning apparatus (such as an electric toothbrush) as shown in FIG. 1, showing the attitude of the head module.
Figure 9:
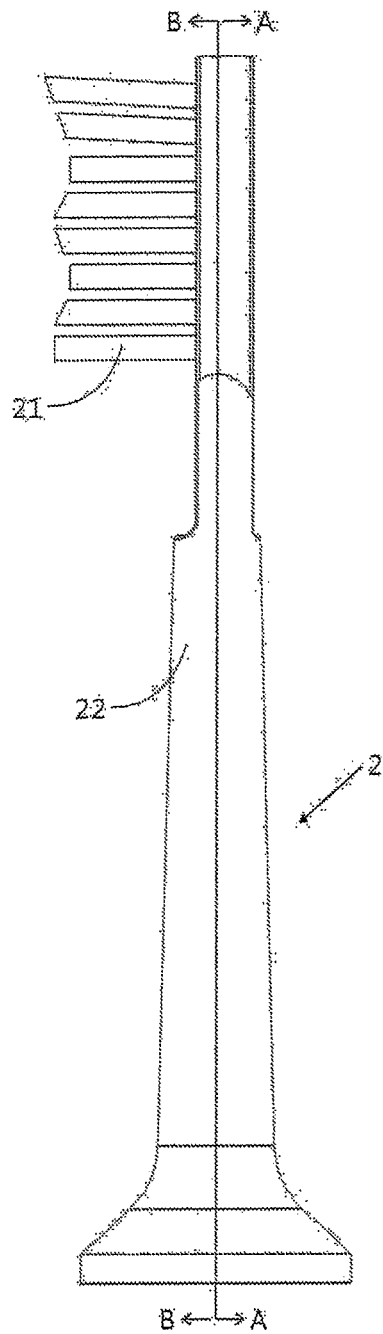
FIG. 9 is a side view of the head module as shown in FIG. 8.
Figure 10:
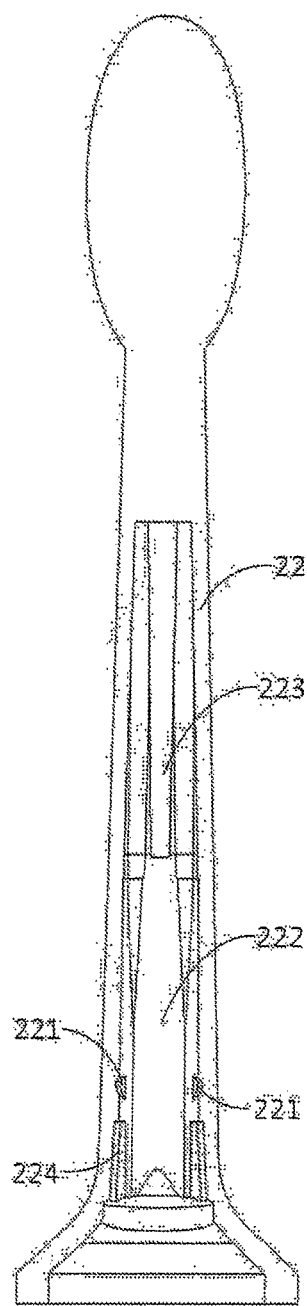
FIG. 10 is a schematic view of the head module housing taken along the A-A direction in FIG. 9.
Figure 11:
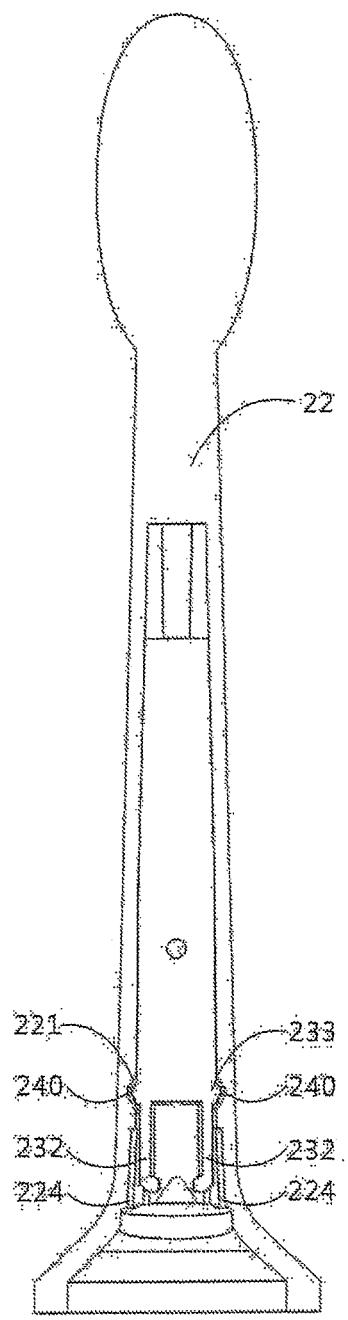
FIG. 11 is a schematic view of the head module as shown in FIG. 8 taken along the A-A direction in FIG. 9.
Figure 12:
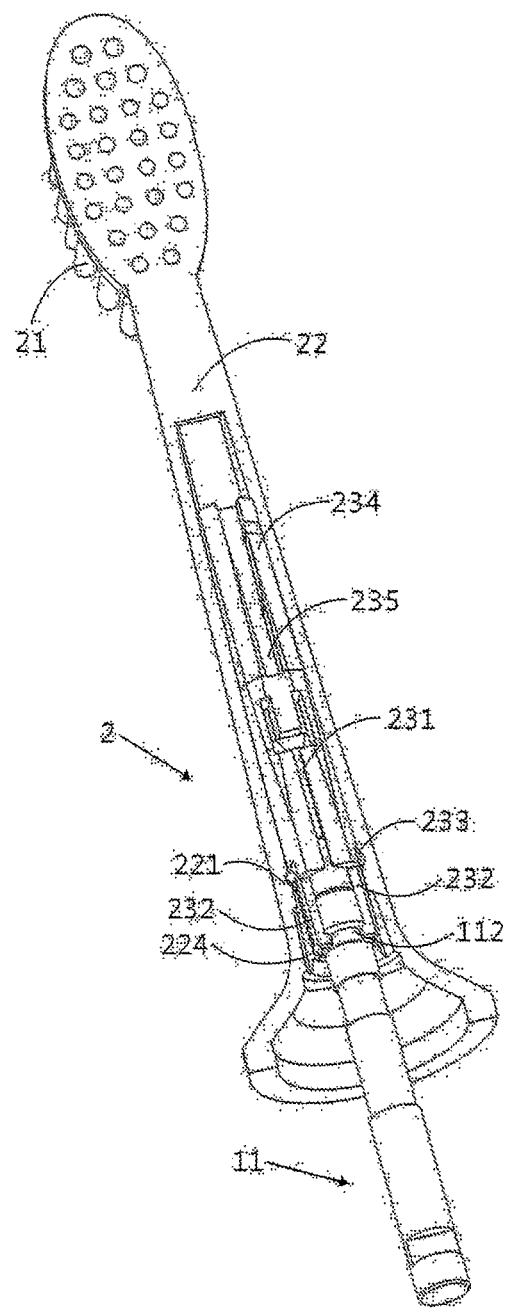
FIG. 12 is a combined schematic view of the head module as shown in FIG. 8 taken along the B-B direction in FIG. 9, including the entire head module driven rod and the entire drive shaft and part of the head module housing.

Referring to FIGS. 5 to 6, the head module driven rod 23 is provided with a hollow cavity body 239 of the head module driven rod, and the hollow cavity body 239 accommodates the drive shaft 11. At least one gap 231 of the head module driven rod is distributed in a region surrounding the hollow cavity body 239 of the head module driven rod, and the gap 231 makes the head module driven rod 23 have elasticity in a radial direction of a cross section of the hollow cavity body 239 of the head module driven rod; two elastic buckles 232 of the head module driven rod are distributed at the lower part of the head module driven rod 23, and the elastic buckles 232 of the head module driven rod may be elastically coupled to a annular groove 112 of the drive shaft. The two elastic buckles 232 have elasticity. Two protrusions 233 of the head module driven rod are distributed on the outside of the head module driven rod 23 near the elastic buckles 232 of the head module driven rod, and the protrusions 233 of the head module driven rod are located below the top end of the gap 231 of the head module driven rod in a direction of the rotation axis $L_1$ of the drive shaft. A first plane 236 of the head module driven rod cooperating with a first plane 111 of the drive shaft is distributed at the periphery of the hollow cavity body 239 of the head module driven rod. Two second planes 237 of the head module driven rod cooperating with the second plane 114 of the drive shaft are distributed at the periphery of the hollow cavity body 239 of the head module driven rod adjacent to the gap 231 of the head module driven rod. A partially cylindrical cavity body region 238 of the head module driven rod cooperating with a cylinder region 113 of the drive shaft on the drive shaft 11 is distributed at the periphery of the hollow cavity body 239 of the head module driven rod. A fixing portion 234 of the head module driven rod and a fixing portion groove 235 of the head module driven rod are distributed in an upper region of the head module driven rod 23. Although in this embodiment, the head module driven rod includes a partially cylindrical cavity body region 238, it is apparent that a conical cavity body region may also be used to replace the cylindrical cavity body region in this embodiment, which also falls into the scope of the present invention. Although in this embodiment, the drive shaft includes part of the cylinder region 113, it is apparent that a cone region may also be used to replace the cylinder region in this embodiment, which also falls into the scope of the present invention.

Referring to FIGS. 7 to 11, the head module housing 22 is provided with a hollow inner cavity 222 of the head module housing for accommodating the head module driven rod 23. The protrusion 223 of the head module housing is distributed in an upper part of the inner cavity 222 of the head module housing so that the protrusion 223 of the head module housing is mechanically fastened to the fixing portion groove 235 of the head module driven rod.

In the present invention, the head module housing 22 and the head module driven rod 23 are both plastic products. The plastic products are suitable for large-volume industrial production and have good economy, but the mechanical fastening force between the plastic products will deteriorate over time due to the creep characteristics of plastic materials, and so the mechanical fastening of simple plastic products cannot be fixed to one another reliably and for a long time.

Therefore, in the present invention, a inner side notch 221 of the head module housing may be distributed on a side wall of the inner cavity 222 of the head module housing, and the inner side notch 221 of the head module housing is used for accommodating a corresponding protrusion 233 of the head module driven rod; the inner side notch 221 of the head module housing restricts the movement of the protrusion 233 of the head module driven rod in a direction of the rotation axis $L_1$ of the drive shaft, and the coupling between the inner side notch 221 and the protrusion 233 of the head module driven rod is achieved by the cooperation of the notch 221 and the protrusion 233, and thus the constraint of the inner side notch 221 of the head module housing on the protrusion 233 of the head module driven rod does not deteriorate over time. Two protrusions 233 of the head module driven rod are symmetrically distributed on the head module driven rod 23 along an axis of the head module housing, and the protrusions 233 of the head module driven rod are located below the top end of the gap 231 of the head module driven rod in a direction of the rotation axis $L_1$ of the drive shaft, and correspondingly the inner side notch (notches) 221 of the head module housing is distributed on the side wall of the inner cavity 222 of the head module housing. Preferably, two inner side notches 221 of the head module housing are symmetrically distributed on the side wall of the inner cavity 222 of the head module housing along an axis of the head module housing. Two buckle grooves 224 of the head module housing are distributed on the side wall of the lower end of the inner cavity 222 of the head module housing to accommodate the elastic buckles 232 of the head module driven rod. The buckle groove 224 of the head module housing can be designed to allow the elastic buckle 232 of the head module driven rod to move in a direction perpendicular to the rotation axis $L_1$ of the drive shaft without interference with the buckle groove 224 of the head module housing.

Figure 13:
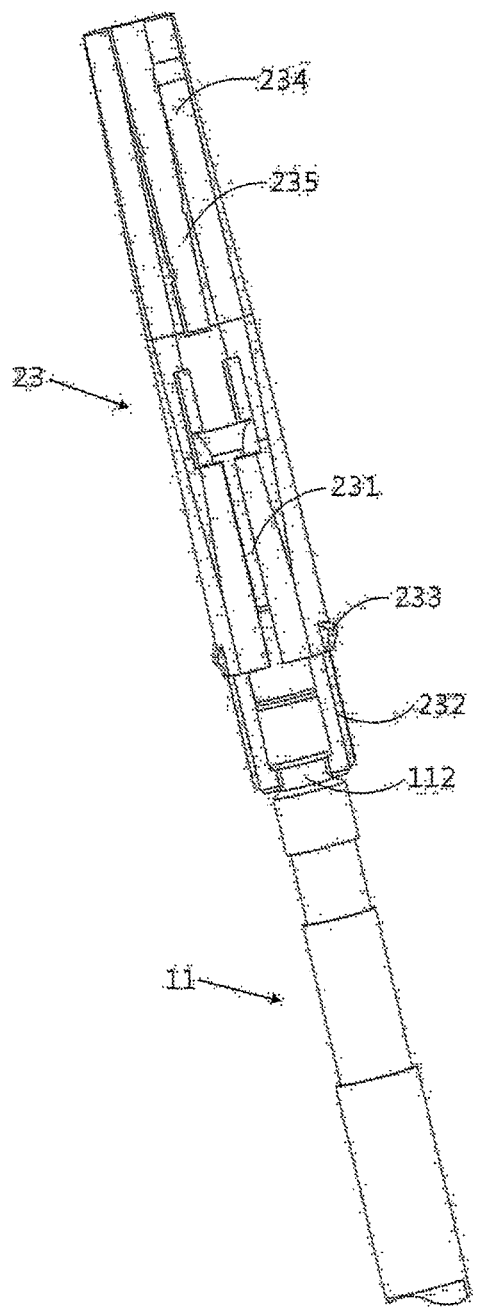
FIG. 13 is a schematic view of the combination of the head module driven rod as shown in FIG. 8 and the drive shaft of the handle.

Referring to FIG. 5 and FIG. 13, in this embodiment, a gap 231 of the head module driven rod is opened in the head module driven rod 23 in a direction of the rotation axis $L_1$ of the drive shaft, and the gap 231 of the head module driven rod can cause the head module driven rod 23 to produce a displacement in a direction perpendicular to the rotation axis $L_1$ of the drive shaft when subjected to an external force or a component force in a direction perpendicular to the rotation axis L1 of the drive shaft. When the external force or component force disappears, the head module driven rod 23 can be restored to the state in which the external force or component force is not applied, based on the elasticity of its own material. This characteristic is referred to in this description as the head module driven rod 23 having elasticity in the direction perpendicular to the rotation axis $L_1$ of the drive shaft. As described above, the head module driven rod 23 is provided with two protrusions 233 of the head module driven rod in the direction perpendicular to the rotation axis $L_1$ of the drive shaft, and the protrusions 233 of the head module driven rod are located below the top end of the gap 231 of the head module driven rod in the direction of the rotation axis $L_1$ of the drive shaft. Similarly, since the head module driven rod 23 is provided with the gap 231 of the head module driven rod, the protrusions 233 of the head module driven rod also have elasticity in a direction perpendicular to the rotation axis $L_1$ of the drive shaft. Obviously, as long as the median line of the gap 231 of the head module driven rod is not perpendicular to the rotation axis $L_1$ of the drive shaft, it can be realized that the head module driven rod 23 has elasticity in a direction perpendicular to the rotation axis $L_1$ of the drive shaft, and that the protrusions 233 of the head module driven rod have elasticity in a direction perpendicular to the rotation axis $L_1$ of the drive shaft. Obviously, a plurality of gaps 231 of the head module driven rod also have the above features, that is, as long as the median lines of the gaps 231 of the head module driven rod are not perpendicular to the rotation axis $L_1$ of the drive shaft, it can be realized that the head module driven rod 23 has elasticity in a direction perpendicular to the rotation axis $L_1$ of the drive shaft, and that the protrusions 233 of the head module driven rod have elasticity in a direction perpendicular to the rotation axis $L_1$ of the drive shaft. The respective median lines of the plurality of gaps 231 of the head module driven rod may be parallel to each other or may also be interlaced with each other, which is not detailed here.

In this case, the width of the gaps 231 of the head module driven rod is 0.3 mm-2 mm, preferably 0.7 mm-1.2 mm.

Referring to FIG. 13, two elastic buckles 232 of the head module driven rod are distributed at the lower part of the head module driven rod 23, and the elastic buckles 232 of the head module driven rod cooperate with an annular groove 112 of the drive shaft. The protrusions at the lower end of the elastic buckles 232 of the head module driven rod can fully or partially enter the annular groove 112 of the drive shaft, thereby restricting a movement of the head module driven rod 23 relative to the drive shaft 11 in a direction of the rotation axis $L_1$ of the drive shaft of the handle.

Referring to FIGS. 3, 4 and 6, as described above, the lower end of the head module driven rod 23 is a hollow cavity body 239 of the head module driven rod, and the cross-sectional contour line of the hollow cavity body 239 of the head module driven rod is roughly composed of a circular arc and two straight line segments, that is, the hollow cavity body 239 of the head module driven rod is roughly surrounded by part of the cylinder side and two planes. The hollow cavity body 239 of the head module driven rod includes a first plane 236 of the head module driven rod, a second plane 237 of the head module driven rod and a partially cylindrical cavity body region 238 of the head module driven rod. The first plane 236 of the head module driven rod cooperates with a first plane 111 of the drive shaft to thereby restrict the rotation of the head module driven rod 23 relative to the draft shaft 11. The second plane 237 of the head module driven rod cooperates with a second plane 114 of the drive shaft to thereby restrict the rotation of the head module driven rod 23 relative to the draft shaft 11. The partially cylindrical cavity body region 238 of the head module driven rod cooperates with a cylinder region 113 of the drive shaft on the drive shaft 11. The first plane 111 of the drive shaft and the second plane 114 of the drive shaft are distributed on the upper end of the drive shaft 11; the first plane 111 of the drive shaft and the second plane 114 of the drive shaft are parallel with each other, and the width of the first plane 111 of the drive shaft or the second plane 114 of the drive shaft in a direction perpendicular to the rotation axis $L_1$ of the drive shaft is 40%-100% of the diameter corresponding to the cylinder region 113 of the drive shaft. Preferably, the width of the first plane 111 of the drive shaft in a direction perpendicular to the rotation axis $L_1$ of the drive shaft is 100% of the diameter corresponding to the width in the cylinder region 113 of the drive shaft, and the width of the second plane 114 of the drive shaft in a direction perpendicular to the rotation axis $L_1$ of the drive shaft is 50% of the diameter corresponding to the width in the cylinder region 113 of the drive shaft. Preferably, the width of the first plane 236 of the head module driven rod cooperating with the first plane 111 of the drive shaft, in a direction perpendicular to the rotation axis $L_1$ of the drive shaft is slightly greater than or equal to the width of the first plane 111 of the drive shaft in the direction perpendicular to the rotation axis $L_1$ of the drive shaft, and the width of the second plane 237 of the head module driven rod cooperating with a second plane 114 of the drive shaft, in a direction perpendicular to the rotation axis $L_1$ of the drive shaft is slightly greater than or equal to the width of the second plane 114 of the drive shaft in the direction perpendicular to the rotation axis $L_1$ of the drive shaft.

Referring to FIGS. 3, 6, 12 and 13, the geometrical dimension of the partially cylindrical cavity body region 238 of the head module driven rod is smaller than the geometrical dimension of the cylinder region 113 of the drive shaft, and the diameter of the partially cylindrical cavity body region 238 of the head module driven rod is smaller than the diameter of the cylinder region 113 of the drive shaft. More specifically, the partially cylindrical cavity body region 238 of the head module driven rod and the cylinder region 113 of the drive shaft belong to an interference fit. In this embodiment, two partially cylindrical cavity body regions 238 of the head module driven rod are symmetrically distributed relative to the rotation axis $L_1$ of the drive shaft, and two cylinder regions 113 of the drive shaft are symmetrically distributed relative to the rotation axis $L_1$ of the drive shaft. Preferably, the diameter of the partially cylindrical cavity body regions 238 of the head module driven rod is 0.02 mm to 2 mm smaller than the diameter of the corresponding cylinder regions 113 of the drive shaft, that is, the amount of single-side interference between the partially cylindrical cavity body region 238 of the head module driven rod and the cylinder region 113 of the drive shaft in a direction perpendicular to the rotation axis $L_1$ of the drive shaft is 0.01 mm to 1 mm. In this description, the aforesaid amount of single-side interference is defined as the amount of single-side interference between the head module driven rod and the drive shaft. Preferably, the amount of single-side interference is 0.20 mm.

The present invention creatively provides at least one inner side notch 221 of the head module housing on the head module housing 22, and provides at least one protrusion 233 of the head module driven rod on the head module driven rod 23, wherein the protrusion 233 of the head module driven rod is located below the top end of the gap 231 of the head module driven rod in a direction of the rotation axis $L_1$ of the drive shaft, and the inner side notches 221 of the head module housing respectively accommodate the corresponding protrusions 233 of the head module driven rod. Obviously, when the drive shaft 11 is not inserted into the head module driven rod 23, there is a gap 240 between the inner side notch 221 of the head module housing and the protrusion 233 of the head module driven rod in a direction perpendicular to the rotation axis $L_1$ of the drive shaft. Preferably, the length of the gap 240 in the direction perpendicular to the rotation axis $L_1$ of the drive shaft is greater than or equal to the amount of single-side interference between the head module driven rod 23 and the drive shaft 11.

The present invention creatively provides at least one gap 231 of the head module driven rod on the head module driven rod 23 in a direction that is not perpendicular to the rotation axis $L_1$ of the drive shaft, and an included angle between a median line of the gap 231 of the head module driven rod and the rotation axis $L_1$ of the drive shaft is greater than −90 degrees and less than 90 degrees. Preferably, the included angle between a median line of the gap 231 of the head module driven rod and the rotation axis $L_1$ of the drive shaft of the handle is greater than −45 degrees and less than 45 degrees, and more preferably, the included angle between a median line of the gap 231 of the head module driven rod and the rotation axis $L_1$ of the drive shaft is zero degree. The respective median lines of the plurality of gaps 231 of the head module driven rod may be parallel to each other or may also be interlaced with each other. The gaps 231 of the head module driven rod make the head module driven rod 23 have elasticity in a direction perpendicular to the rotation axis $L_1$ of the drive shaft, and make the protrusions 233 of the head module driven rod have elasticity in a direction perpendicular to the rotation axis $L_1$ of the drive shaft.

To sum up, according to the present invention, there is an interference between the partially cylindrical cavity body region 238 of the head module driven rod and the cylinder region 113 of the drive shaft in a direction perpendicular to the rotation axis $L_1$ of the drive shaft, and the amount of single-side interference of the interference is called the amount of single-side interference between the head module driven rod and the drive shaft of the handle. The amount of single-side interference between the head module driven rod and the drive shaft is 0.01 mm to 1 mm, while the gaps 231 of the head module driven rod make the protrusions 233 of the head module driven rod have elasticity in a direction perpendicular to the rotation axis $L_1$ of the drive shaft, and the inner side notches 221 of the head module housing accommodate the protrusions 233 of the head module driven rod. When the drive shaft 11 is not inserted into the head module driven rod 23, a length of the gap 240 between the head module housing 22 and the head module driven rod 23 in the direction perpendicular to the rotation axis $L_1$ of the drive shaft is greater than or equal to the amount of single-side interference between the head module driven rod and the drive shaft.

When the drive shaft 11 is inserted into the head module driven rod 23, since there exists the amount of single-side interference between the head module driven rod and the drive shaft, and due to the elasticity of the protrusion 233 of the head module driven rod formed by the gap 231 of the head module driven rod and the cooperation between the inner side notch 221 of the head module housing and the protrusion 233 of the head module driven rod, the drive shaft 11 can push the protrusion 233 of the head module driven rod deeper into the inner side notch 221 of the head module housing so that the inner side notch 221 of the head module housing more reliably restricts the movement of the protrusion 233 of the head module driven rod along the rotation axis $L_1$ of the drive shaft, thereby ensuring that when the drive shaft 11 is inserted into the head module 2 and starts to drive the head module 2 to make a reciprocal rotation movement, the head module driven rod 23 is undetachably held in the head module housing 22, thereby effectively preventing the head module housing 22 from flying out of the head module driven rod 23 during the movement to injure a user.

Referring to FIGS. 3, 4, 6, 12 and 13, when the drive shaft 11 is inserted into the head module driven rod 23, since there exists the amount of single-side interference between the head module driven rod 23 and the drive shaft 11, and due to the elasticity of the protrusion 233 of the head module driven rod formed by the gap 231 of the head module driven rod and the cooperation between the inner side notch 221 of the head module housing and the protrusion 233 of the head module driven rod, the drive shaft 11 drives the protrusion 233 of the head module driven rod to move in a direction deeper into the inner side notch 221 of the head module housing; the first plane 236 of the head module driven rod and the second plane 237 of the head module driven rod distributed on the head module driven rod 23 move toward or more closely fitted to their respectively matched first plane 111 of the drive shaft and second plane 114 of the drive shaft located on the drive shaft 11, thereby increasing the pressure and friction between the head module driven rod 23 and the drive shaft 11. During the movement of the head module, the increased friction helps the head module driven rod 23 to always maintain a stable coupling with the drive shaft 11, thereby preventing the head module 2 from flying out of the drive shaft 11 during the movement to injure the user.

What is claimed is:

1. A combination of a handle portion and a head module (2) of an electric cleaning apparatus, the handle portion comprises a handle (1) accommodating a driving portion therein, and a drive shaft (11) in the handle (1) extending upward out of the handle (1) in a direction of the rotation axis ($L_1$) of the drive shaft (11) and reciprocally rotating around the rotation axis ($L_1$) of the drive shaft (11), the head module (2) detachably coupled to the handle (1), and the drive shaft (11) driving the head module (2) to reciprocally rotate around the rotation axis ($L_1$) of the drive shaft;

the head module (2) comprises cleaning elements (21), a head module housing (22) and a head module driven rod (23) disposed in a hollow inner cavity (222) of the head module housing (22); the head module driven rod (23) is provided with a hollow cavity body (239) of the head module driven rod for accommodating the drive shaft (11), wherein at least one gap (231) of the head module driven rod is provided in a region surrounding the hollow cavity body (239) so that the head module driven rod (23) has elasticity in a radial direction of a cross section of the hollow cavity body (239) of the head module driven rod; at least one inner side notch (221) of the head module housing is distributed on a side wall of the inner cavity (222) of the head module housing, and the inner side notch (221) is used for accommodating a corresponding protrusion (233) of the head module driven rod that is disposed on the head module driven rod (23) so that the inner side notch (221) of the head module housing restricts a movement of the protrusion (233) of the head module driven rod in a direction of the rotation axis ($L_1$) of the drive shaft; the head module driven rod (23) further comprises a partially cylindrical or conical cavity body region (238), and a diameter of the cylindrical or conical cavity body region (238) or the greatest diameter of a corresponding joining portion is less than a diameter of a cylinder or conoid region (113) of the drive shaft or the greatest diameter of a corresponding joining portion, both being an interference fit; when the drive shaft (11) is not yet inserted into the head module driven rod (23), there is a gap (240) between the inner side notch (221) of the head module housing and the protrusion (233) of the head module driven rod in a direction perpendicular to the rotation axis ($L_1$) of the drive shaft, and a length of the gap (240) in the direction perpendicular to the rotation axis ($L_1$) of the drive shaft is greater than or equal to an amount of single-side interference between the head module driven rod (23) and the drive shaft (11); the amount of single-side interference is 0.01 mm to 1 mm.

2. The combination according to claim 1, wherein the gap (231) of the head module driven rod is distributed on the head module driven rod (23) in a direction that is not perpendicular to the rotation axis ($L_1$) of the drive shaft.

3. The combination according to claim 2, wherein the inner side notch (221) of the head module housing is disposed on a side wall of the inner cavity (222) of the head module housing.

4. The combination according to claim 2, wherein the protrusion (233) of the head module driven rod is located below the top end of the gap (231) of the head module driven rod in a direction of the rotation axis ($L_1$) of the drive shaft.

5. The combination according to claim 2, wherein two protrusions (233) of the head module driven rod are symmetrically distributed on the head module driven rod (23) along an axis of the head module housing, and the protrusions (233) of the head module driven rod are located below the top end of the gap (231) of the head module driven rod in a direction of the rotation axis ($L_1$) of the drive shaft, and correspondingly two inner side notches (221) of the head module housing are symmetrically distributed on the side wall of the inner cavity (222) of the head module housing along an axis of the head module housing.

6. The combination according to claim 2, wherein a width of the gap (231) of the head module driven rod is 0.3 mm-2 mm.

7. The combination according to claim 2, wherein each component of the head module (2) is all made of plastic.

8. The combination according to claim 2, wherein two elastic buckles (232) of the head module driven rod with protrusions at the lower end of the elastic buckles (232) are distributed at the lower part of the head module driven rod (23), and the elastic buckles (232) cooperate with an annular groove (112) of the drive shaft disposed on the drive shaft (11) so that the protrusions at the lower end of the elastic buckles (232) can fully or partially enter the annular groove (112) of the drive shaft, thereby restricting a movement of the head module driven rod (23) relative to the drive shaft (11) in a direction of the rotation axis ($L_1$) of the drive shaft of the handle.

9. The combination according to claim 2, wherein an included angle between a median line of the gap (231) of the head module driven rod and the rotation axis ($L_1$) of the drive shaft is greater than −90 degrees and less than 90 degrees.

10. The combination according to claim 9, wherein a width of the gap (231) of the head module driven rod is 0.3 mm-2 mm.

11. The combination according to claim 9, wherein the included angle between a median line of the gap (231) of the head module driven rod and the rotation axis ($L_1$) of the drive shaft is greater than −45 degrees and less than 45 degrees.

12. The combination according to claim 11, wherein the included angle between a median line of the gap (231) of the head module driven rod and the rotation axis ($L_1$) of the drive shaft is zero degree.

13. The combination according to claim 11, wherein a width of the gap (231) of the head module driven rod is 0.3 mm-2 mm.

14. The combination according to claim 12, wherein a width of the gap (231) of the head module driven rod is 0.3 mm-2 mm.

15. The combination according to claim 1, wherein the inner side notch (221) of the head module housing is disposed on a side wall of the inner cavity (222) of the head module housing.

16. The combination according to claim 1, wherein the protrusion (233) of the head module driven rod is located below the top end of the gap (231) of the head module driven rod in a direction of the rotation axis ($L_1$) of the drive shaft.

17. The combination according to claim 1, wherein two protrusions (233) of the head module driven rod are symmetrically distributed on the head module driven rod (23) along an axis of the head module housing, and the protrusions (233) of the head module driven rod are located below the top end of the gap (231) of the head module driven rod in a direction of the rotation axis ($L_1$) of the drive shaft, and correspondingly two inner side notches (221) of the head module housing are symmetrically distributed on the side wall of the inner cavity (222) of the head module housing along an axis of the head module housing.

18. The combination according to claim 1, wherein the amount of single-side interference is 0.20 mm.

19. The combination according to claim 1, wherein a width of the gap (231) of the head module driven rod is 0.3 mm-2 mm.

20. The combination according to claim 19, wherein the width of the gap (231) of the head module driven rod is 0.7 mm-1.2 mm.

21. The combination according to claim 1, wherein each component of the head module (2) is all made of plastic.

22. The combination according to claim 1, wherein two elastic buckles (232) of the head module driven rod with protrusions at the lower end of the elastic buckles (232) are distributed at the lower part of the head module driven rod (23), and the elastic buckles (232) cooperate with an annular groove (112) of the drive shaft disposed on the drive shaft (11) so that the protrusions at the lower end of the elastic buckles (232) can fully or partially enter the annular groove (112) of the drive shaft, thereby restricting a movement of the head module driven rod (23) relative to the drive shaft (11) in a direction of the rotation axis ($L_1$) of the drive shaft of the handle.

* * * * *